US012721345B2

(12) United States Patent
Ding et al.

(10) Patent No.: US 12,721,345 B2
(45) Date of Patent: Sep. 1, 2026

(54) ULTRAFINE GOLD NANOCOMPOSITE, AND PREPARATION METHOD AND USE THEREOF

(71) Applicant: Innovation Center of Yangtze River Delta, ZJU, Jiaxing City (CN)

(72) Inventors: Tian Ding, Hangzhou (CN); Mofei Shen, Hangzhou (CN); Jinsong Feng, Hangzhou (CN); Xinyu Liao, Hangzhou (CN); Yunlei Xianyu, Hangzhou (CN); Meimei Guo, Hangzhou (CN); Pengfei Ge, Hangzhou (CN)

(73) Assignee: Innovation Center of Yangtze River Delta, ZJU, Jiaxing City (CN)

( * ) Notice: Subject to any disclaimer, the term of this patent is extended or adjusted under 35 U.S.C. 154(b) by 298 days.

(21) Appl. No.: 18/506,895

(22) Filed: Nov. 10, 2023

(65) Prior Publication Data

US 2025/0089721 A1 Mar. 20, 2025

(30) Foreign Application Priority Data

Sep. 18, 2023 (CN) ........................ 202311203275.0

(51) Int. Cl.

| | |
|---|---|
| ***A61K 31/724*** | (2006.01) |
| ***A01N 25/10*** | (2006.01) |
| ***A01N 59/16*** | (2006.01) |
| ***A01P 1/00*** | (2006.01) |
| ***A61K 33/242*** | (2019.01) |

(52) U.S. Cl.

CPC ............. *A01N 59/16* (2013.01); *A01N 25/10* (2013.01); *A01P 1/00* (2021.08); *A61K 33/242* (2019.01)

(58) Field of Classification Search

CPC .................. A01N 59/16; A61K 33/242; A23V 2250/1568; A23V 2250/5112

See application file for complete search history.

(56) References Cited

U.S. PATENT DOCUMENTS

2005/0153071 A1* 7/2005 Bouvrette ................ B22F 9/24 977/755

OTHER PUBLICATIONS

Zhao et al. JACS, 2016, 138, 16645-16654.*
Zhao et al., JACS, 2016, supporting information S1-S32.*
Gamma-Cyclodextrin, Pubmed, 2 pgs.*
Hammami et al., J King Saud Uni, 33, 2021, 1-10.*
Anderson et al., J Nanopart Res, 2011, 13, 2843-2851.*
Prochowicz et al., Chemical Reviews, 2017, 117, 13461-13501.*

* cited by examiner

*Primary Examiner* — Kyle A Purdy
(74) *Attorney, Agent, or Firm* — Bochner PLLC; Andrew D. Bochner

(57) ABSTRACT

Provided are an ultrafine gold nanocomposite, and a preparation method and use thereof. The preparation method of the ultrafine gold nanocomposite includes the following steps: mixing a cyclodextrin metal-organic framework (CD-MOF) material, chloroauric acid and a solvent to obtain a mixture, and subjecting the mixture to incubation to obtain the ultrafine gold nanocomposite.

11 Claims, 15 Drawing Sheets

ULTRAFINE GOLD NANOCOMPOSITE, AND PREPARATION METHOD AND USE THEREOF

CROSS REFERENCE TO RELATED APPLICATION

This patent application claims the benefit and priority of Chinese Patent Application No. 2023112032750 filed with the China National Intellectual Property Administration on Sep. 18, 2023, the disclosure of which is incorporated by reference herein in its entirety as part of the present application.

TECHNICAL FIELD

The present disclosure relates to the technical field of functional materials, in particular to an ultrafine gold nanocomposite, and a preparation method and use thereof.

BACKGROUND

Nanoparticles are effective biocides with broad-spectrum bactericidal effects. The nanoparticles act on cell walls and cell membranes, destroy membrane structures and membrane potential, inhibit a combination of tRNA with ribosome small subunits, and hinder synthesis of proteins. Since nanoparticles have numerous mechanisms of action and targets inside and outside cells, it is less likely that microorganisms could develop drug resistance to nanoparticles. Gold nanoparticles have high stability, low cytotoxicity, and high biocompatibility in various environments. However, the antibacterial effect of the gold nanoparticles is affected by their sizes. Studies have shown that the gold nanoparticles with a smaller particle size show higher antibacterial activity.

The gold nanoparticles prepared by traditional methods have a larger particle size of mainly 12 nm to 14 nm, and exhibit a weak antibacterial activity. However, when the gold nanoparticles with smaller particle sizes are prepared by traditional methods, harmful reagents (such as sodium borohydride and hydrazine hydrate) are adopted in general, which are easy to remain in the prepared gold nanoparticles, thereby limiting their application in the fields of food and medicine.

SUMMARY

An object of the present disclosure is to provide an ultrafine gold nanocomposite, and a preparation method and use thereof. In the present disclosure, the ultrafine gold nanocomposite has a desirable antibacterial effect, and the preparation method thereof does not adopt harmful reagents, and thus is safe and environmental-friendly; furthermore, an antibacterial product prepared by the ultrafine gold nanocomposite shows a wide range of applications.

To achieve the above object, the present disclosure provides the following technical solutions:

Provided is a method for preparing an ultrafine gold nanocomposite, including the following steps:

mixing a cyclodextrin metal-organic framework (CD-MOF) material, chloroauric acid and a solvent to obtain a mixture; and subjecting the mixture to incubation to obtain the ultrafine gold nanocomposite.

In some embodiments, the CD-MOF material is prepared from raw materials including γ-cyclodextrin (γ-CD).

In some embodiments, an amount of the CD-MOF material is based on an amount of the γ-CD; a molar ratio of the γ-CD to the chloroauric acid is in a range of 2.5:1 to 20:1; and a ratio of an amount of substance of the chloroauric acid to a volume of the solvent is in a range of 1.25 mmol: 1 L to 1.5 mmol: 1 L.

In some embodiments, the incubation is conducted at a temperature of 25° C. to 37° C. for 3 h to 24 h.

In some embodiments, the incubation is conducted under oscillation at a speed of 10 rpm to 240 rpm.

In some embodiments, the incubation is conducted in the dark.

Also provided is an ultrafine gold nanocomposite prepared by the method described above, including a CD-MOF material and ultrafine gold nanoparticles loaded on the CD-MOF material.

In some embodiments, the ultrafine gold nanoparticles have a particle size of 1 nm to 3 nm.

In some embodiments, a loading rate of the ultrafine gold nanoparticles in the ultrafine gold nanocomposite is in a range of 0.18 wt % to 2.33 wt %.

Also provided is use of the ultrafine gold nanocomposite in preparation of an antibacterial product.

The present disclosure provides a method for preparing an ultrafine gold nanocomposite, including the following steps: mixing a CD-MOF material, chloroauric acid and a solvent to obtain a mixture; and subjecting the mixture to incubation to obtain the ultrafine gold nanocomposite. The ultrafine gold nanocomposite has a desirable antibacterial effect, and the preparation method thereof does not adopt harmful reagents, and thus is safe and environmental-friendly; furthermore, an antibacterial product prepared by the ultrafine gold nanocomposite shows a wide range of applications. Specifically, the ultrafine gold nanoparticles are loaded on the CD-MOF material, and the obtained ultrafine gold nanocomposite still retains desirable antibacterial properties of the ultrafine gold nanoparticles. The antibacterial product prepared by the ultrafine gold nanocomposite shows a wide range of applications, such as in food, medicine, environment and other fields.

Furthermore, the ultrafine gold nanocomposite is prepared by an oscillating method, which has mild reactions and simple operations.

DETAILED DESCRIPTION OF THE EMBODIMENTS

Figure 1A:
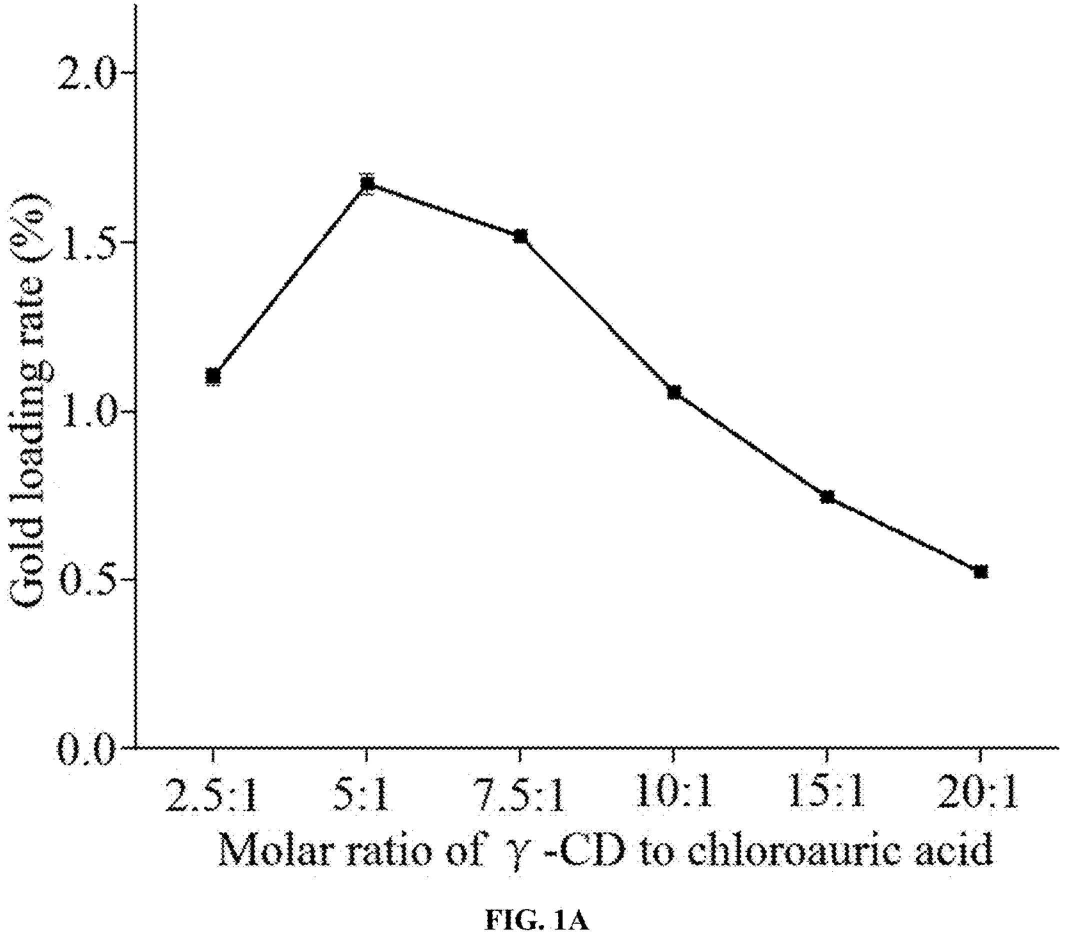
FIG. 1A shows an influence of a molar ratio of the γ-CD to chloroauric acid on the loading rate of the ultrafine gold nanoparticles when preparing Au@CD-MOF according to an embodiment of the present disclosure.

The present disclosure provides a method for preparing an ultrafine gold nanocomposite, including the following steps:

mixing a cyclodextrin metal-organic framework (CD-MOF) material, chloroauric acid and a solvent to obtain a mixture; and subjecting the mixture to incubation to obtain the ultrafine gold nanocomposite.

In the present disclosure, the ultrafine gold nanoparticles are loaded on the CD-MOF material, and the obtained ultrafine gold nanocomposite still retains desirable antibacterial properties of the ultrafine gold nanoparticles. The antibacterial product prepared by the ultrafine gold nanocomposite shows a wide range of applications, such as in food, medicine, environment and other fields. Metal-Organic Frameworks (MOFs), also known as porous coordination polymers, are a new type of porous hybrid materials composed of multidentate organic ligands and metal ions or metal clusters, and have adjustable topological structures, excellent porosity, and large specific surface area, making it possible to show broad application prospects in the field of material loading and delivery. Cyclodextrin (CD) is a natural cyclic oligosaccharide composed of 6 to 12 D-glucopyranose units. Different numbers of D-glucopyranose units (6, 7, and 8) are ligated by α-1,4 glycosidic bonds, corresponding to different CD molecules (α-CD, β-CD, and γ-CD). Due to the three-dimensional arrangement of glucose units, the CD has a three-dimensional porous structure similar to a hollow cylinder, such that nanoparticles and other chemical substances could be loaded inside its cavity. Cyclodextrin metal-organic framework (CD-MOF), a new MOF, made of CD and alkali metal ions through organic coordination is in the form of a uniform cube, where a center of the cube contains a spherical cavity with a diameter of about 1.7 nm, and a channel diameter is about 0.78 nm (specifically taking the CD-MOF prepared by γ-CD as an example). Therefore, the size of an internal cavity of the CD-MOF could limit the growth of gold nanoparticles. In addition, compared with traditional MOF, the CD-MOF also has desirable water solubility and non-toxicity, and shows properties of porosity and large specific surface area. Moreover, the cavity of the CD-MOF has a loading effect. In the present disclosure, with the help of an ultra-small pore size of the CD-MOF (including a spherical cavity with a diameter of about 1.7 nm, and a channel diameter of about 0.78 nm), the growth of gold nanoparticles is restricted, such that the ultrafine gold nanoparticles are obtained with a particle size of 1 nm to 3 nm and a desirable antibacterial effect. Moreover, the method for loading the ultrafine gold nanoparticles by the CD-MOF material has a mild reaction, simple operations, and no pollution to the environment. The ultrafine gold nanocomposite prepared by the method of the present disclosure has uniform appearance, better crystal characteristics of XRD peaks, desirable thermal stability, and excellent antibacterial effect.

In some embodiments, the CD-MOF material is prepared from raw materials including γ-CD. In some embodiments, the CD-MOF material is prepared by a method including the following steps:

mixing the γ-CD, an alkali metal compound, water and an organic solvent to obtain a mixed material; and subjecting the mixed material to coordination to obtain a coordination product liquid; and mixing the coordination product liquid and a surfactant to obtain an admixture; and subjecting the admixture to crystallization to obtain the CD-MOF material.

In the present disclosure, the γ-CD, the alkali metal compound, water and the organic solvent are mixed to obtain the mixed material, and the mixed material is subjected to coordination, to obtain the coordination product liquid. In some embodiments, the alkali metal compound includes an alkali metal hydroxide or an alkali metal chloride; the alkali metal hydroxide includes potassium hydroxide, rubidium hydroxide, or cesium hydroxide; and the alkali metal chloride includes potassium chloride or cesium chloride. In some embodiments, a molar ratio of the γ-CD to an alkali metal element in the alkali metal compound is in a range of 1:(5-10), and preferably 1:(9-10). The alkali metal compound provides an alkali metal ion as a metal center to allow the coordination to finally form a coordination bond. Specifically, potassium hydroxide is taken as an example. Generally, potassium ions in the CD-MOF material are in a form of 8-coordination, making 6 γ-CDs form a minimum building unit of the CD-MOF, which is equivalent to 2 potassium ions paired with 1 γ-CD, with a chemical formula of [(C48H80O40)(KOH)2]n. In addition, excess potassium hydroxide is conducive to the participation of all γ-CDs in the reaction. In some embodiments, the organic solvent includes methanol, ethanol, or acetone. There is no special limitation on dosages of the organic solvent and water, and any dosages of the organic solvent and water that could ensure a smooth reaction could be used.

In some embodiments, the γ-CD, the alkali metal compound, and water are mixed, ultrasonically dissolved, and filtered through a 0.45 μm water-based filter membrane, and an obtained filtrate is mixed with the organic solvent to obtain the mixed material, and the mixed material is subjected to coordination. In some embodiments, the coordination is conducted at a temperature of 80° C. to 100° C., and preferably 90° C. In some embodiments, the coordination is conducted for 3 min to 7 min, and preferably 5 min. In some embodiments, the coordination is conducted under stirring at a speed of 300 rpm to 500 rpm, and preferably 400 rpm.

In the present disclosure, after the coordination, no post-treatment is required, and the coordination product liquid is directly mixed with a surfactant to obtain the admixture, and the admixture is subjected to crystallization to obtain the CD-MOF material. In some embodiments, the surfactant includes polyethylene glycol, cetyltrimethylammonium bromide, or triethylamine, where the polyethylene glycol has a molecular weight of 8,000. In some embodiments, a molar ratio of the surfactant to the γ-CD is in a range of (0.06-0.07):1. In some embodiments, the coordination product liquid is mixed with the surfactant, stirred at a temperature of 80° C. to 100° C. (preferably 90° C.) for 10 min to 15 min, and stood at a temperature of 20° C. to 30° C. (preferably 24° C.) in a cold water bath for 10 h to 15 h (preferably 12 h) to precipitate a white precipitate in the system. Then the white precipitate is subjected to solid-liquid separation, and an obtained precipitate is washed and dried in sequence to obtain the CD-MOF material. There is no special limitation on a method of the solid-liquid separation, and methods well known to those skilled in the art could be used, such as centrifugal separation. In some embodiments, the washing is conducted by methanol by centrifugal washing 2 to 3 times. In some embodiments, the drying is vacuum drying at a temperature of 55° C. to 65° C., and preferably 60° C. In some embodiments, the drying is performed for 4 h to 6 h, and preferably 5 h.

In the present disclosure, after the CD-MOF material is obtained, the CD-MOF material is mixed with chloroauric acid and the solvent to obtain the mixture, and the mixture is subjected to incubation to obtain the ultrafine gold nanocomposite. In some embodiments, an amount of the CD-MOF material is based on an amount of the γ-CD (1 mol of the CD-MOF material contains 6 mol of the γ-CD), and a molar ratio of the γ-CD to the chloroauric acid is in a range of (2.5-20):1, preferably (3-15):1, more preferably (4-10):1, and even more preferably (5-7.5):1. In some embodiments, the solvent is an organic solvent, and the organic solvent is acetonitrile or methanol, and preferably the acetonitrile. In some embodiments, a ratio of an amount of substance of the chloroauric acid to a volume of the solvent is in a range of (1.25-1.5) mmol:1 L, and preferably 1.25 mmol:1 L.

In some embodiments, the chloroauric acid is mixed with the solvent, and then an obtained chloroauric acid solution is mixed with the CD-MOF material to obtain the mixture, and the mixture is subjected to incubation. In some embodiments, the incubation is conducted at a temperature of 25° C. to 37° C., and preferably 33° C. to 37° C. In some embodiments, the incubation is conducted for 3 h to 24 h, preferably 6 h to 23.5 h, more preferably 9 h to 23 h, even more preferably 12 h to 22.5 h, still more preferably 15 h to 22 h, and still more preferably 18 h to 21 h. In some embodiments, the incubation is conducted under oscillation at a speed of 10 rpm to 240 rpm, preferably 30 rpm to 180 rpm, and more preferably 60 rpm to 120 rpm. In some embodiments, the incubation is conducted in the dark. During the incubation, a large amount of hydroxyl (—OH) in the CD-MOF material act as a reducing agent to reduce gold ions from a trivalent state to a zero valent state.

In some embodiments, after the incubation, an obtained incubation liquid is subjected to solid-liquid separation, and an obtained solid is sequentially washed and dried to obtain the ultrafine gold nanocomposite. There is no special limitation on a method of the solid-liquid separation, and a centrifugal separation could be used. In some embodiments, the centrifugal separation is conducted at a speed of 4,000 rpm to 5,000 rpm, and preferably 5,000 rpm. In some embodiments, the centrifugal separation is conducted for 5 min to 10 min, and preferably 5 min to 8 min. In some embodiments, the washing is conducted by acetonitrile by centrifugal washing 1 to 2 times. Operating conditions of the centrifugal washing are the same as those of the centrifugal separation, and will not be repeated here. In some embodiments, the drying is vacuum drying, and the drying is performed at a temperature of 50° C. to 60° C., and preferably 55° C. to 60° C. In some embodiments, the drying is performed for 2 h to 3 h, and preferably 2 h to 2.5 h.

The present disclosure further provides an ultrafine gold nanocomposite prepared by the method described above, including a CD-MOF material and ultrafine gold nanoparticles loaded on the CD-MOF material. In some embodiments, the ultrafine gold nanoparticles have a particle size of 1 nm to 3 nm. In some embodiments, a loading rate of the ultrafine gold nanoparticles in the ultrafine gold nanocomposite is in a range of 0.18 wt % to 2.33 wt %. In the examples, a loading rate of the ultrafine gold nanoparticles in the ultrafine gold nanocomposite is 0.18 wt %, 0.36 wt %, 0.54 wt %, 0.76 wt %, 1.07 wt %, 1.12 wt %, 1.53 wt %, 1.56 wt %, 1.61 wt %, 1.69 wt %, 1.79 wt %, 2.00 wt %, 2.20 wt %, 2.21 wt %, 2.26 wt %, and 2.33 wt %.

The present disclosure further provides use of the ultrafine gold nanocomposite in preparation of an antibacterial product. In some embodiments, the antibacterial product includes an antibacterial package or an antibacterial drug. There is no special limitation on a preparation method of the antibacterial product, and a method well known to those skilled in the art could be used. There is no special limitation on a specific application field of the antibacterial product. In the method for preparing the ultrafine gold nanocomposite, no harmful reagents are used. The antibacterial product prepared by the ultrafine gold nanocomposite shows a wide range of applications, such as in food, medicine, environment and other fields.

The technical solutions of the present disclosure will be clearly and completely described below with reference to the examples of the present disclosure. Apparently, the described examples are merely a part rather than all of the examples of the present disclosure. All other embodiments obtained by those skilled in the art based on the embodiments of the present disclosure without creative efforts shall fall within the scope of the present disclosure.

In the following examples, the CD-MOF material used was prepared by:

(1) adding γ-CD (2,592 mg, 2 mmol), potassium hydroxide (1,024 mg, 18.24 mmol), and ultrapure water (80 mL) into a beaker, oscillating evenly with an ultrasonic cleaning machine at ambient temperature (25° C.), and then filtering with a 0.45 μm water-based filter membrane to obtain a solution 1;

(2) pre-placing methanol (48 mL) and a rotor in a clean conical beaker, and adding the solution 1 into the conical beaker to obtain a milky white solution 2; sealing the conical beaker with a sealing film, putting the conical beaker into a water bath at 90° C., and stirring the milky white solution 2 by the rotor at a speed of 400 rpm to allow a reaction for 5 min to obtain a clear and transparent solution 3;

(3) adding a surfactant polyethylene glycol (PEG-8000, 1024 mg) quickly into the solution 3 to obtain a milky white solution 4, and stirring the milky white solution 4 for 10 min to make the milky white solution 4 clear and transparent;

(4) sealing the conical beaker with a sealing film and standing the conical beaker in a cold water bath at 24° C. for 12 h to precipitate a white precipitate in the reaction system, subjecting the white precipitate to a first centrifugation with methanol at 5,000 rpm for 5 min, discarding a resulting supernatant, and dispersing a remaining white precipitate in methanol, and subjecting the resulting system to a second centrifugation 2 times under the same conditions as the first centrifugation; and (5) putting the precipitate obtained by the second centrifugation into a vacuum drying oven, drying at 60° C. for 5 h under vacuum conditions, and cooling to ambient temperature to obtain the CD-MOF material.

Examples 1 to 17

In Examples 1 to 17, specifically, an ultrafine gold nanocomposite was prepared according to the conditions shown in Table 1 (the conditions not mentioned in Table 1 were all with reference to Example 15). In Example 15, an ultrafine gold nanocomposite was prepared by the following procedures:

46.56 mg of a CD-MOF material was placed in 5 mL of a chloroauric acid-acetonitrile solution with a concentration of 1.25 mM, and then incubated in the dark at 37° C. and 60 rpm with oscillation on a shaker for 21 h; and an obtained incubation liquid was centrifuged at 5,000 rpm for 5 min, a supernatant was discarded, a remaining material was resuspended in acetonitrile, centrifuged again under the same conditions, a newly obtained supernatant was discarded, and an obtained precipitate was vacuum-dried at 60° C. for 2 h to obtain an ultrafine gold nanoparticles-loaded CD-MOF material (denoted as Au@CD-MOF).

Table 1 Conditions for preparing Au@CD-MOFs in Examples 1 to 17 and the loading rate of the ultrafine gold nanoparticles

| Example | Molar ratio of γ-CD to chloroauric acid | Incubation time (h) | Oscillation rate (rpm) | Au loading rate in Au@CD-MOF (wt %) |
|---|---|---|---|---|
| 1 | 2.5:1 | 12 | 180 | 1.12 ± 0.02 |
| 2 | 5:1 | 12 | 180 | 1.69 ± 0.03 |
| 3 | 7.5:1 | 12 | 180 | 1.53 ± 0.01 |
| 4 | 10:1 | 12 | 180 | 1.07 ± 0.01 |
| 5 | 15:1 | 12 | 180 | 0.76 ± 0.00 |
| 6 | 20:1 | 12 | 180 | 0.54 ± 0.01 |
| 7 | 5:1 | 3 | 180 | 0.18 ± 0.01 |
| 8 | 5:1 | 6 | 180 | 0.36 ± 0.00 |
| 9 | 5:1 | 9 | 180 | 1.07 ± 0.04 |
| 10 | 5:1 | 15 | 180 | 1.56 ± 0.05 |
| 11 | 5:1 | 18 | 180 | 2.00 ± 0.09 |
| 12 | 5:1 | 21 | 180 | 2.26 ± 0.04 |
| 13 | 5:1 | 24 | 180 | 1.79 ± 0.01 |
| 14 | 5:1 | 21 | 10 | 1.61 ± 0.08 |
| 15 | 5:1 | 21 | 60 | 2.20 ± 0.03 |
| 16 | 5:1 | 21 | 120 | 2.21 ± 0.05 |
| 17 | 5:1 | 21 | 240 | 2.33 ± 0.06 |

Figure 1B:
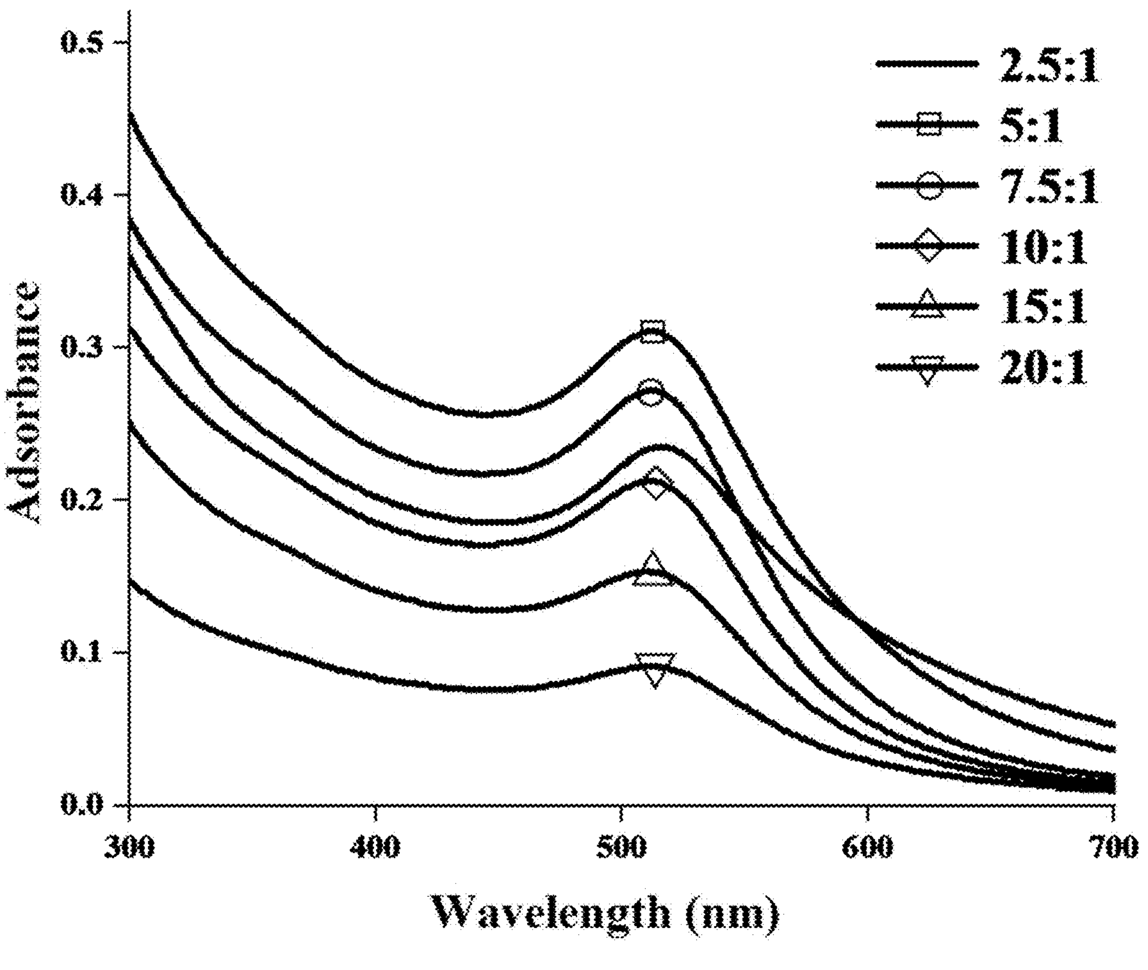
FIG. 1B shows an influence of a molar ratio of the γ-CD to chloroauric acid on UV absorption of the ultrafine gold nanoparticles when preparing Au@CD-MOF according to an embodiment of the present disclosure.

FIG. 1A shows an influence of the molar ratio of γ-CD to chloroauric acid (Examples 1 to 6) on the loading rate of the ultrafine gold nanoparticles when preparing Au@CD-MOF; and FIG. 1B shows an influence of the molar ratio of γ-CD to chloroauric acid (Examples 1 to 6) on UV absorption of the ultrafine gold nanoparticles when preparing Au@CD-MOF. From FIG. 1A and FIG. 1B, it can be seen that the loading rate of the ultrafine gold nanoparticles increases and then decreases. When the molar ratio of γ-CD to chloroauric acid is 5:1, the maximum loading rate of the ultrafine gold nanoparticles could be obtained, at 1.69%±0.03%; while the corresponding UV absorption chart has a larger peak near 520 nm when the molar ratio is 5:1.

Figure 2A:
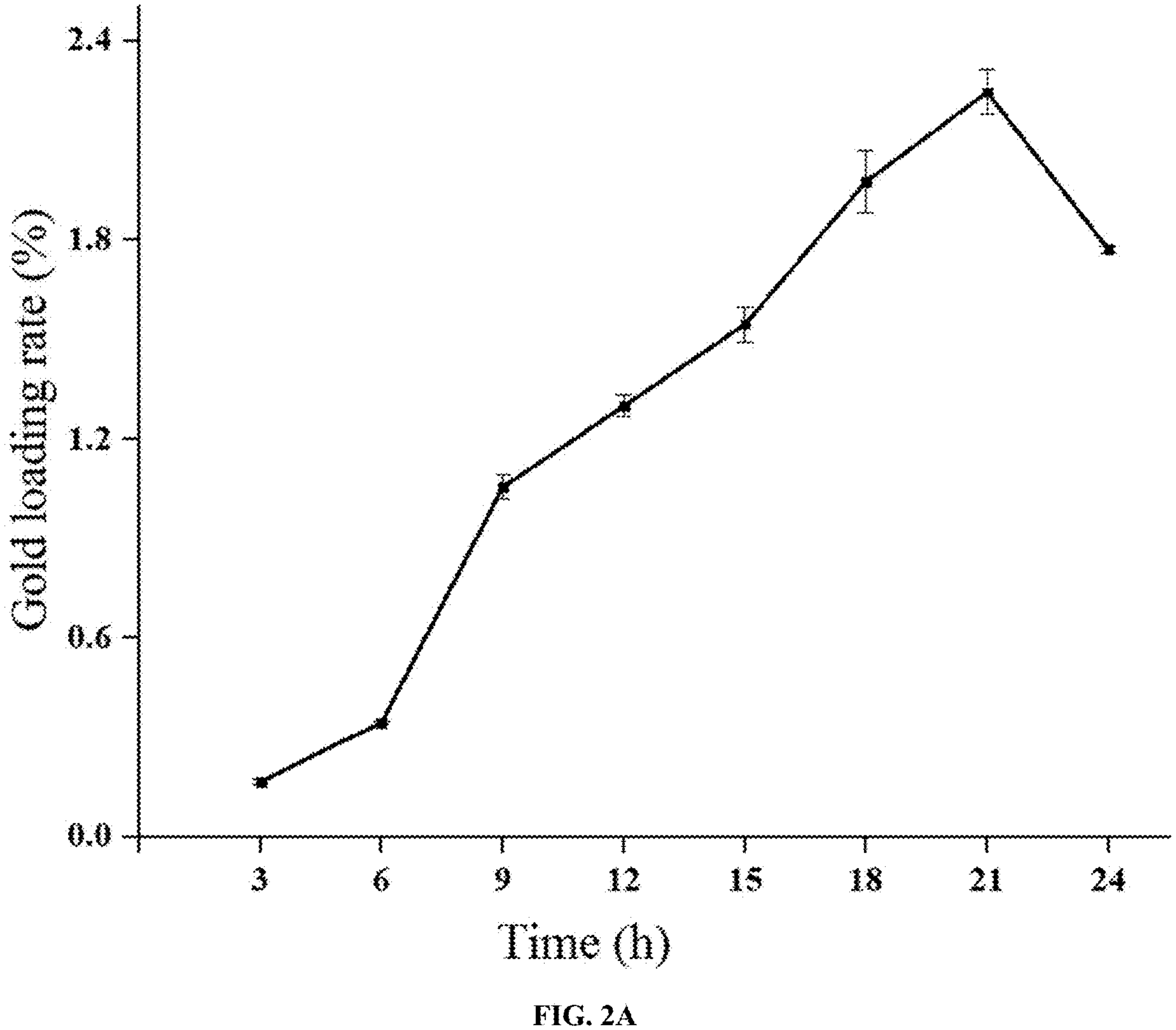
FIG. 2A shows an influence of an incubation time on the loading rate of the ultrafine gold nanoparticles when preparing Au@CD-MOF according to an embodiment of the present disclosure.
Figure 2B:
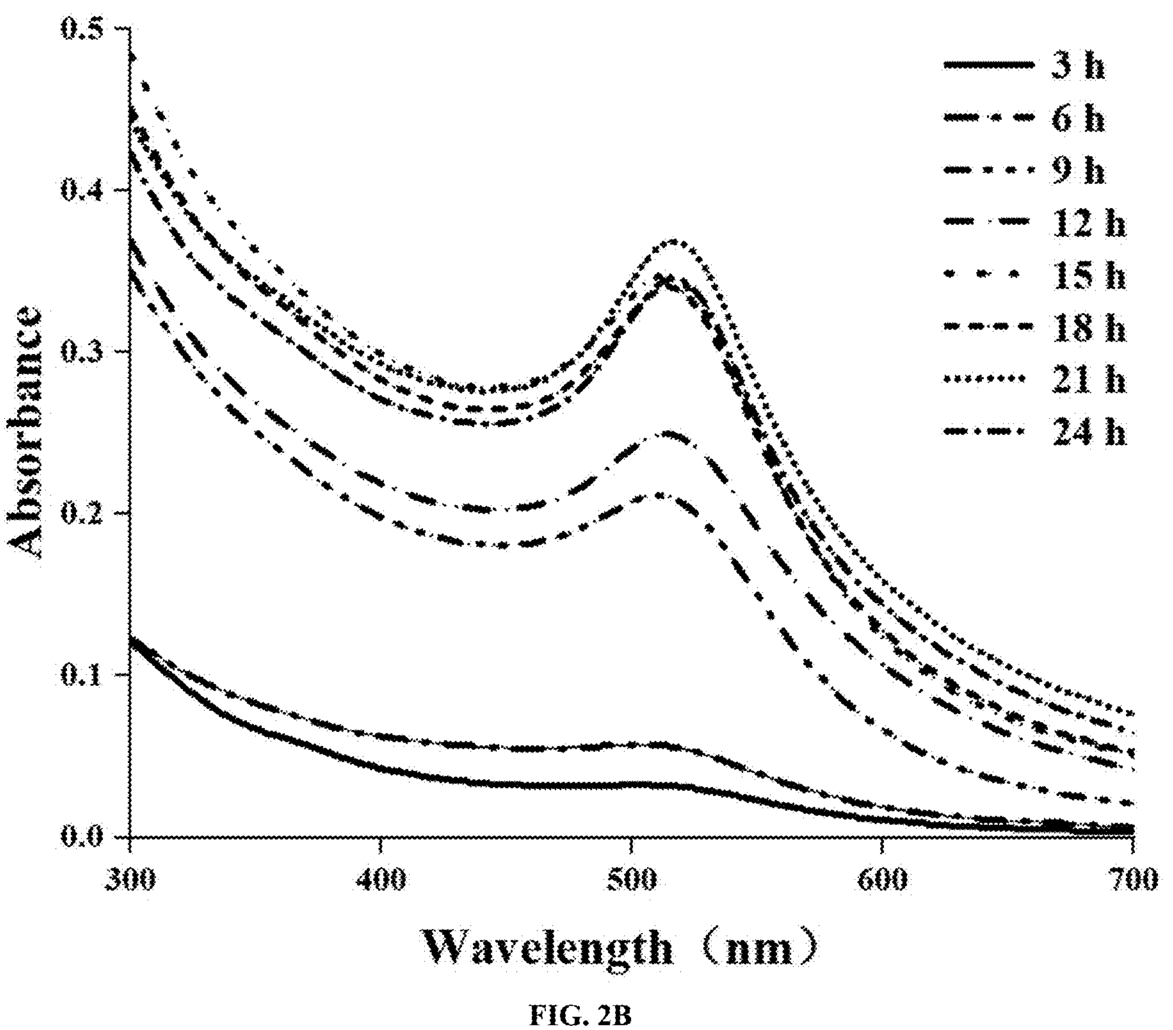
FIG. 2B shows an influence of an incubation time on UV absorption of the ultrafine gold nanoparticles when preparing Au@CD-MOF according to an embodiment of the present disclosure.

FIG. 2A shows an influence of the incubation time (Examples 2 and 7 to 13) on the loading rate of the ultrafine gold nanoparticles when preparing Au@CD-MOF; and FIG. 2B shows an influence of the incubation time (Examples 2 and 7 to 13) on UV absorption of the ultrafine gold nanoparticles when preparing Au@CD-MOF. From FIG. 2A and FIG. 2B, it can be seen that the loading rate of the ultrafine gold nanoparticles increases and then decreases. When the incubation time is 21 h, the maximum loading rate of the ultrafine gold nanoparticles could be obtained, at 2.26%±0.07%; while the corresponding UV absorption chart has a relatively large peak near 520 nm when the incubation time is 21 h.

Figure 3A:
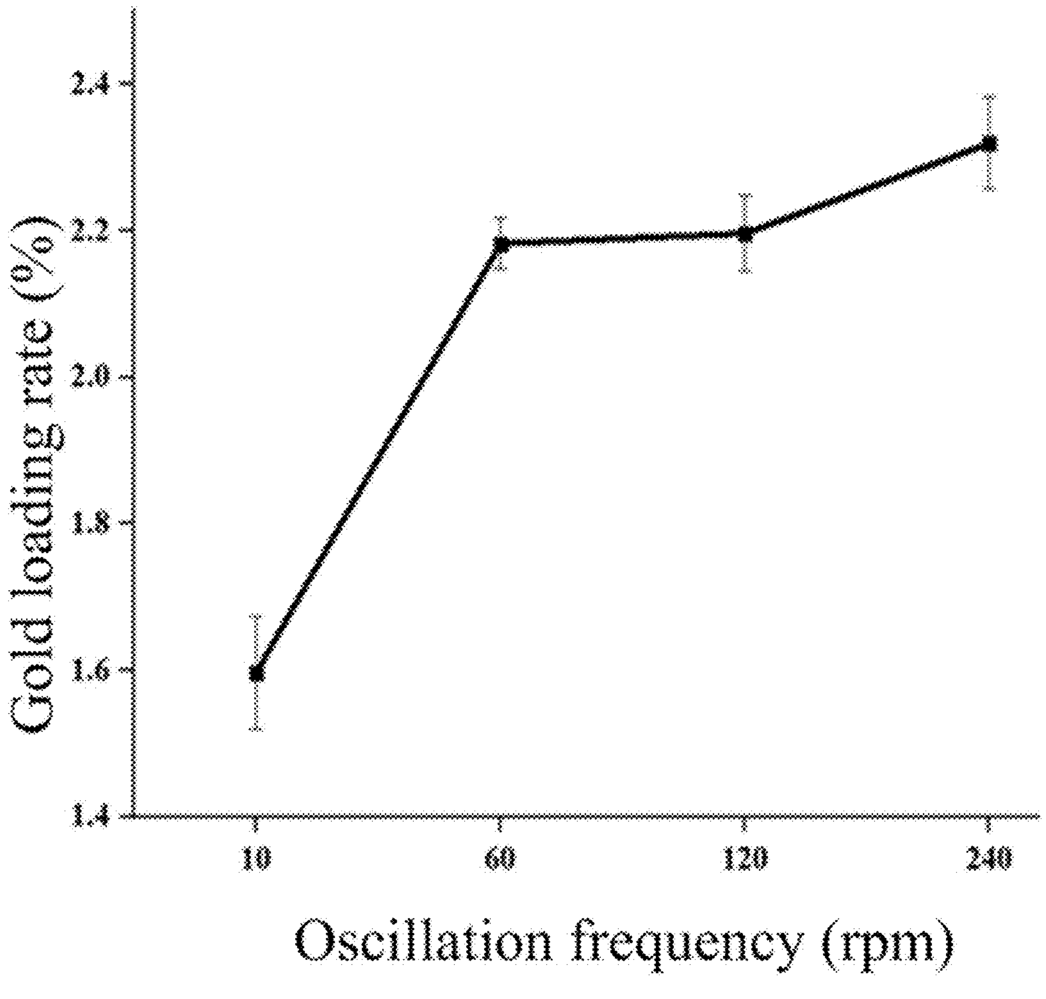
FIG. 3A shows an influence of an oscillation rate on the loading rate of the ultrafine gold nanoparticles when preparing Au@CD-MOF according to an embodiment of the present disclosure.
Figure 3B:
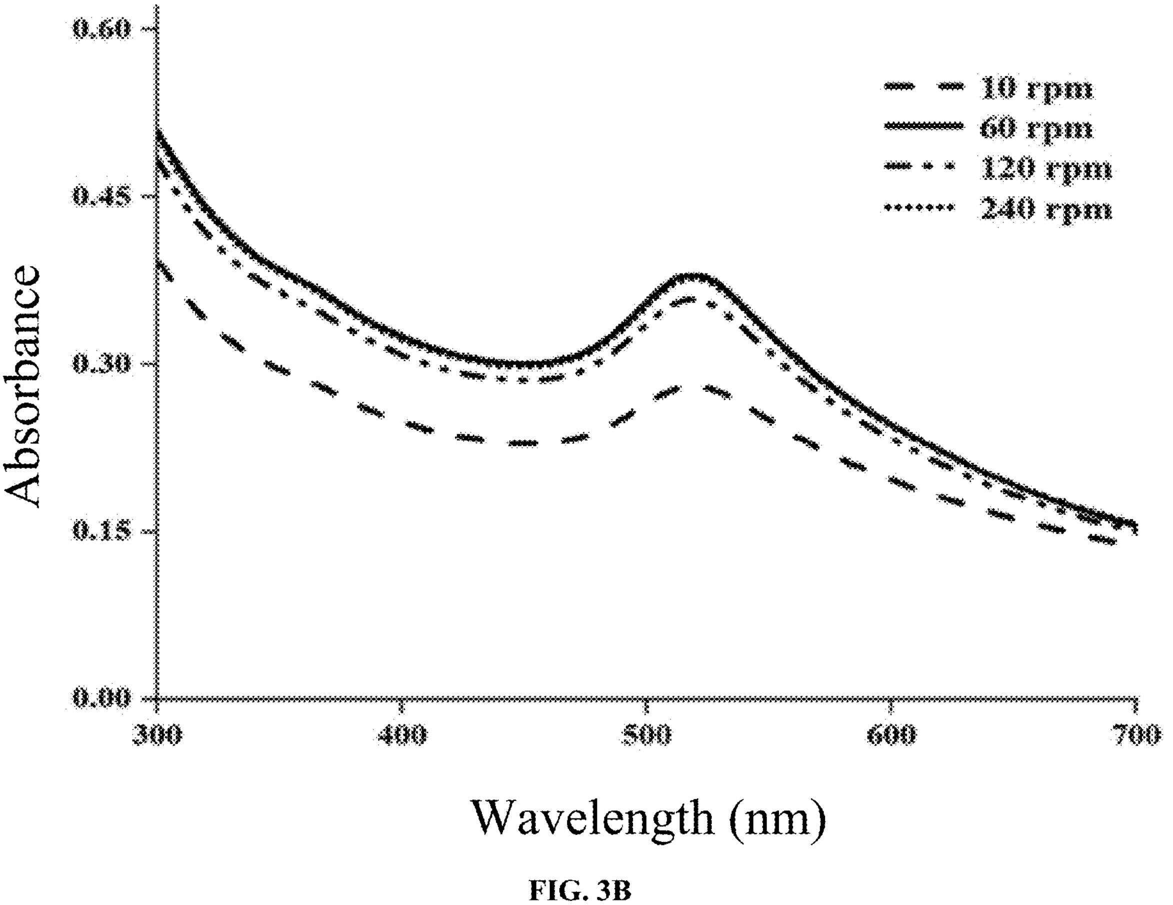
FIG. 3B shows an influence of an oscillation rate on UV absorption of the ultrafine gold nanoparticles when preparing Au@CD-MOF according to an embodiment of the present disclosure.

FIG. 3A shows an influence of the oscillation rate (Examples 12 and 14 to 17) on the loading rate of the ultrafine gold nanoparticles when preparing Au@CD-MOF; and FIG. 3B shows an influence of the oscillation rate (Examples 12 and 14 to 17) on UV absorption of the ultrafine gold nanoparticles when preparing Au@CD-MOF. From FIG. 3A and FIG. 3B, it can be seen that the oscillation rate shows less influence on the ultrafine gold nanoparticles. When the oscillation rate is 60 rpm, the loading rate of the ultrafine gold nanoparticles could be obtained, at 2.20%±0.03%; while the corresponding UV absorption chart has a relatively large peak near 520 nm when the oscillation rate is 60 rpm.

Comparative Example 1

A traditional gold nanoparticle was prepared according to the following procedures:

0.5 mL of a 1 wt % chloroauric acid aqueous solution and 49 mL of ultrapure water were added into a three-neck round bottom flask, and boiled for 5 min at 120° C. under stirring at a speed of 120 rpm. Then 0.5 mL of a sodium citrate aqueous solution with a concentration of 5 wt % was quickly added thereto, and the resulting substance was subjected to reaction. When a resulting reaction system turned to wine red, the system was stood and cooled to ambient temperature, and then stored in the dark at 4° C.

The materials prepared in Example 15 and Comparative Example 1 were characterized, and the specific results are as follows:

An ultraviolet spectrum of the Au@CD-MOF prepared in Example 15 dispersed in water is shown in FIG. 3B (corresponding to the case where the oscillation rate is 60 rpm). The results show that there is an obvious characteristic peak of gold near 520 nm, indicating that the gold nanoparticles are generated in the CD-MOF.

Figure 4A:
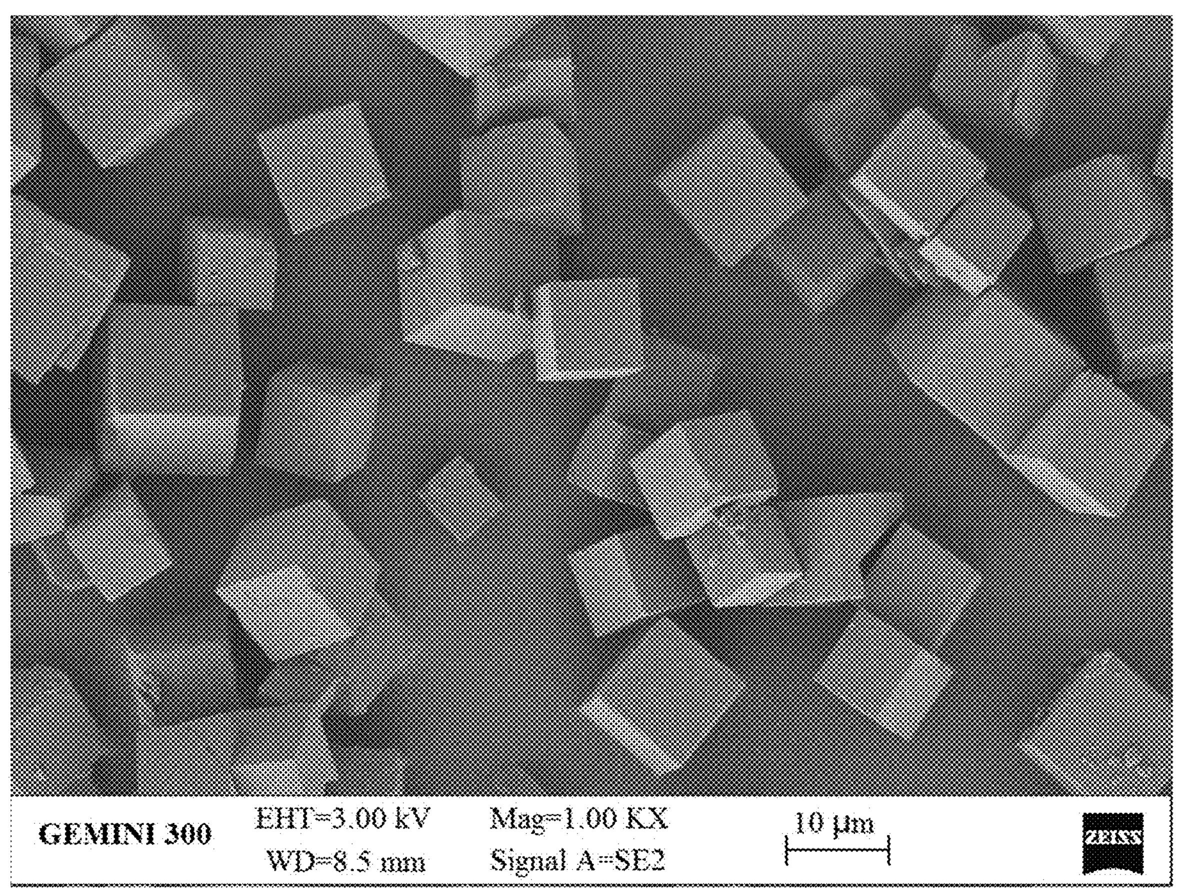
FIG. 4A shows a scanning electron microscopy (SEM) image of CD-MOF.
Figure 4B:
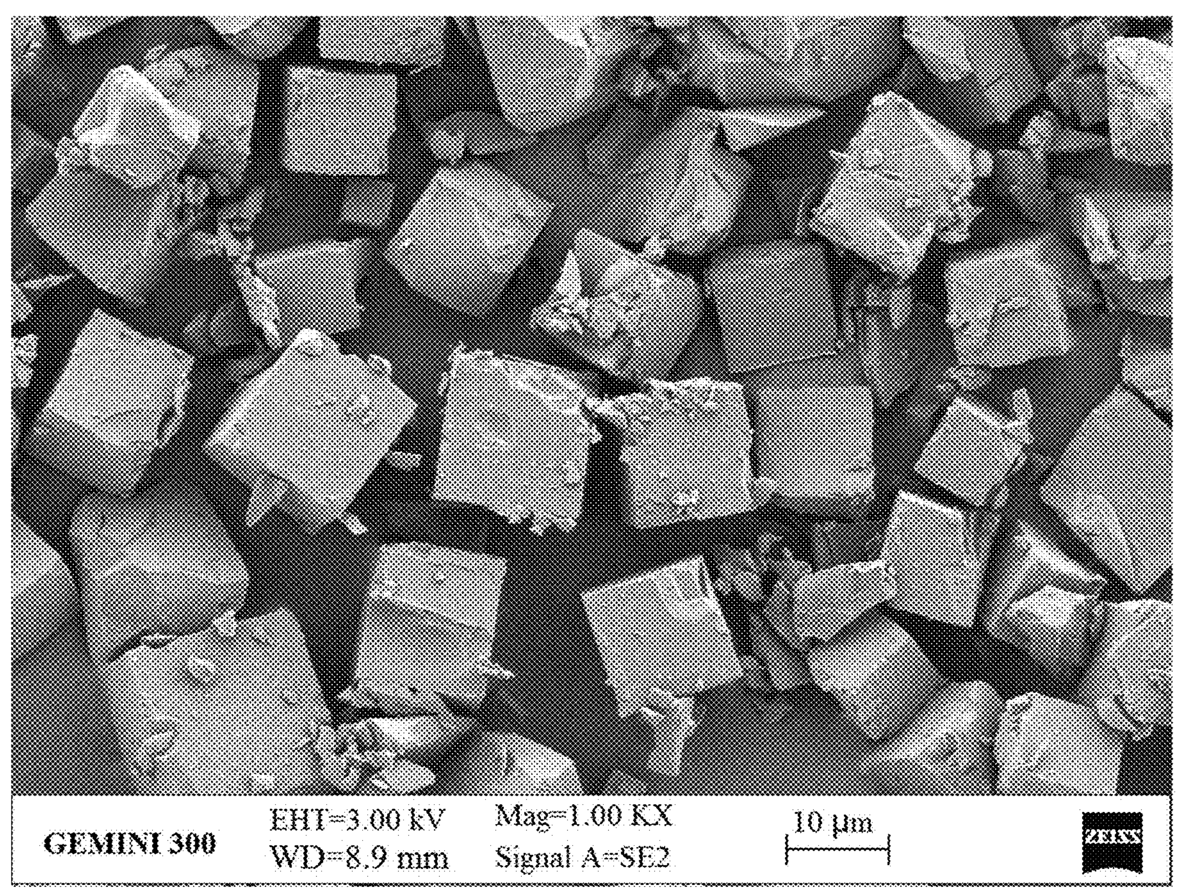
FIG. 4B shows an SEM image of Au@CD-MOF prepared in Example 15.

FIG. 4A shows an SEM image of CD-MOF; and FIG. 4B shows an SEM image of Au@CD-MOF prepared in Example 15. The results show that gold ions are reduced within the CD-MOF framework to generate the ultrafine gold nanoparticles, the structure of CD-MOF is almost not damaged, and Au@CD-MOF still maintains the inherent cubic shape of CD-MOF.

Figure 5:
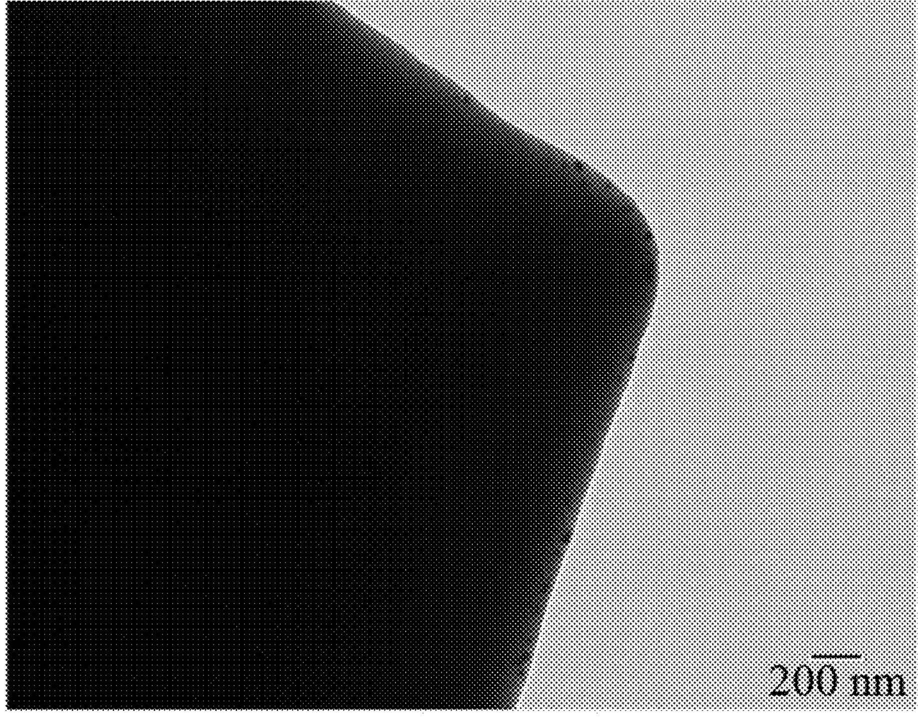
FIG. 5 shows a transmission electron microscopy (TEM) image of Au@CD-MOF prepared in Example 15.

FIG. 5 shows a TEM image of Au@CD-MOF prepared in Example 15. Under the TEM, it can be clearly seen that the ultrafine gold nanoparticles with uniform distribution and even particles appear on a structure edge of the Au@CD-MOF.

Figure 6:
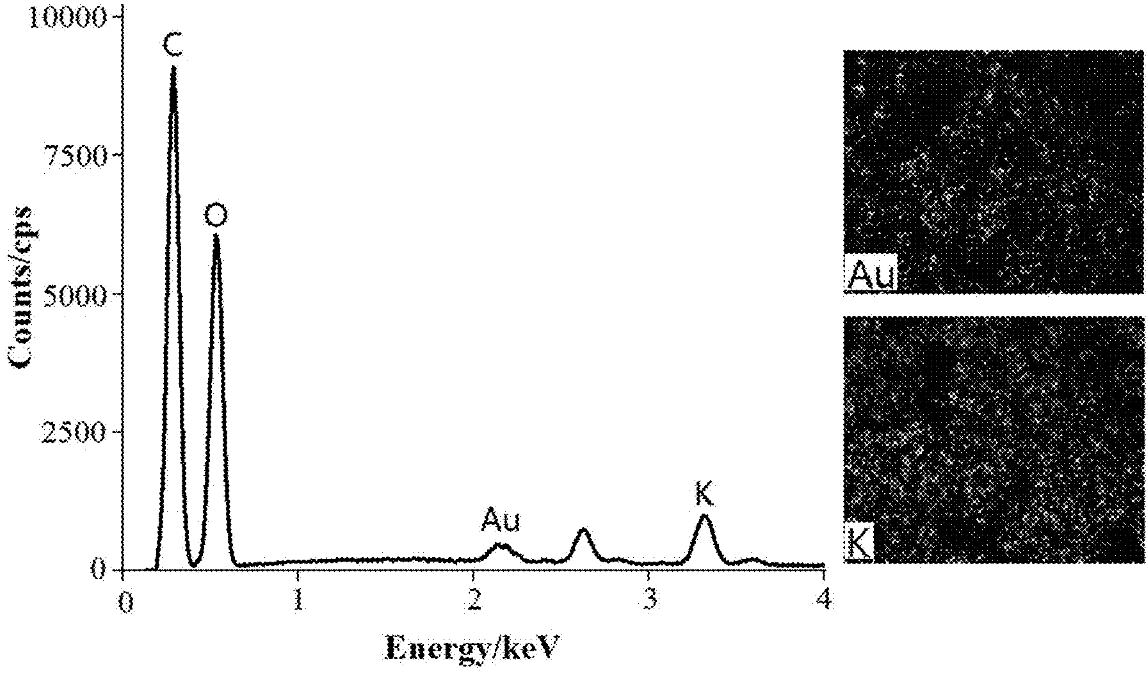
FIG. 6 shows an energy spectrogram of Au@CD-MOF prepared in Example 15.

FIG. 6 shows an energy spectrum of Au@CD-MOF prepared in Example 15. The results show that the gold element representing the gold nanoparticles and the potassium element representing the CD-MOF have consistent distributions, indicating that the ultrafine gold nanoparticles are successfully generated and evenly distributed within the CD-MOF framework.

Figure 7:
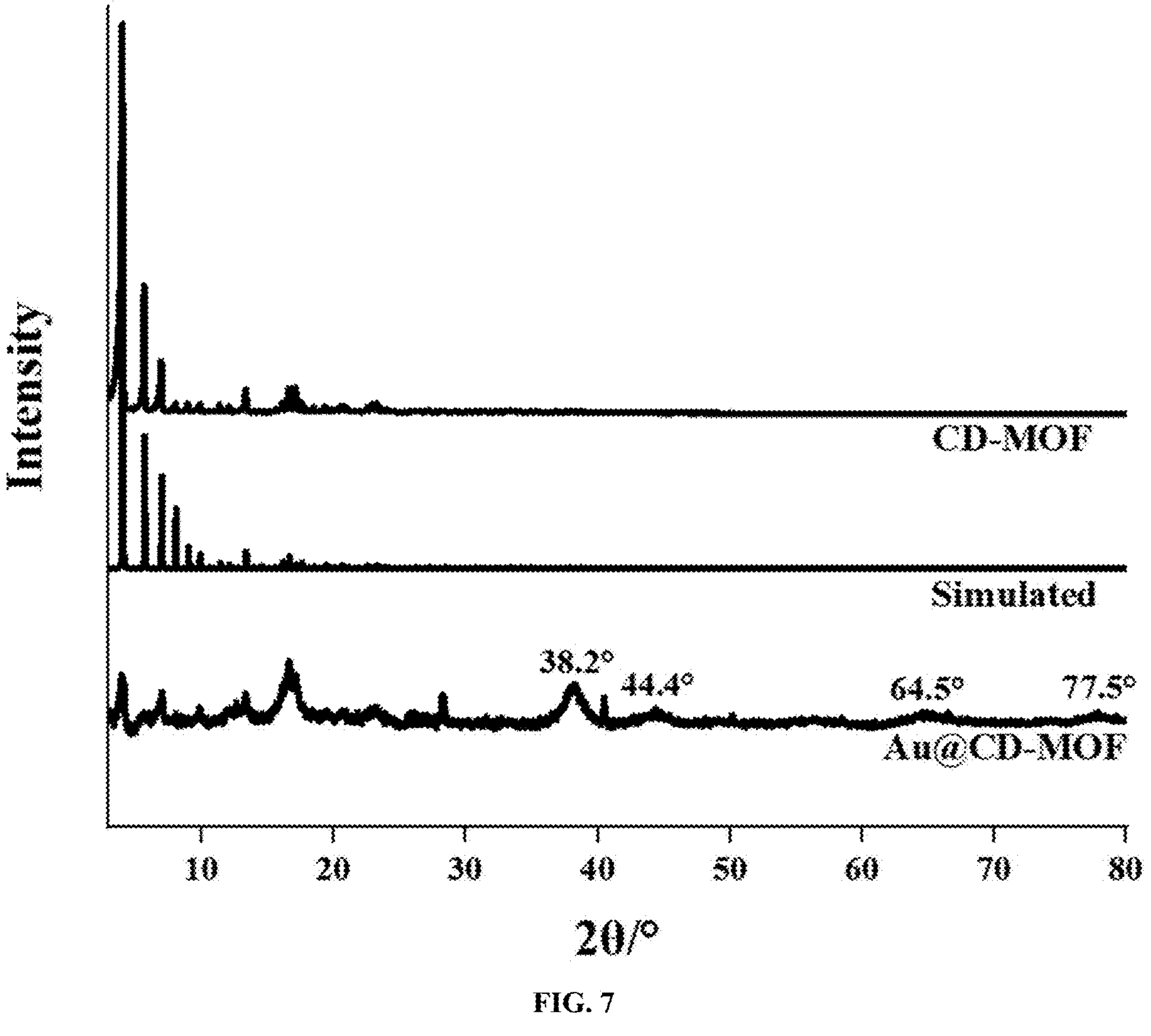
FIG. 7 shows a powder X-ray diffraction (PXRD) pattern of Au@CD-MOF prepared in Example 15.

FIG. 7 shows a PXRD pattern of Au@CD-MOF prepared in Example 15. The results show that a peak position of the spectrum is basically consistent with that of the CD-MOF, indicating that the structure of CD-MOF is almost not damaged in preparing Au@CD-MOF. The 4 diffraction peaks appearing at 2θ at 38.20°, 44.40°, 64.50°, and 77.50° are all characteristic diffraction peaks of gold, which are corresponding to the Au (111), (200), (220), and (311) crystal planes of a face-centered cubic (FCC) structure, respectively. From this, it can be confirmed that the ultrafine gold nanoparticles is successfully prepared in Au@CD-MOF.

Figure 8:
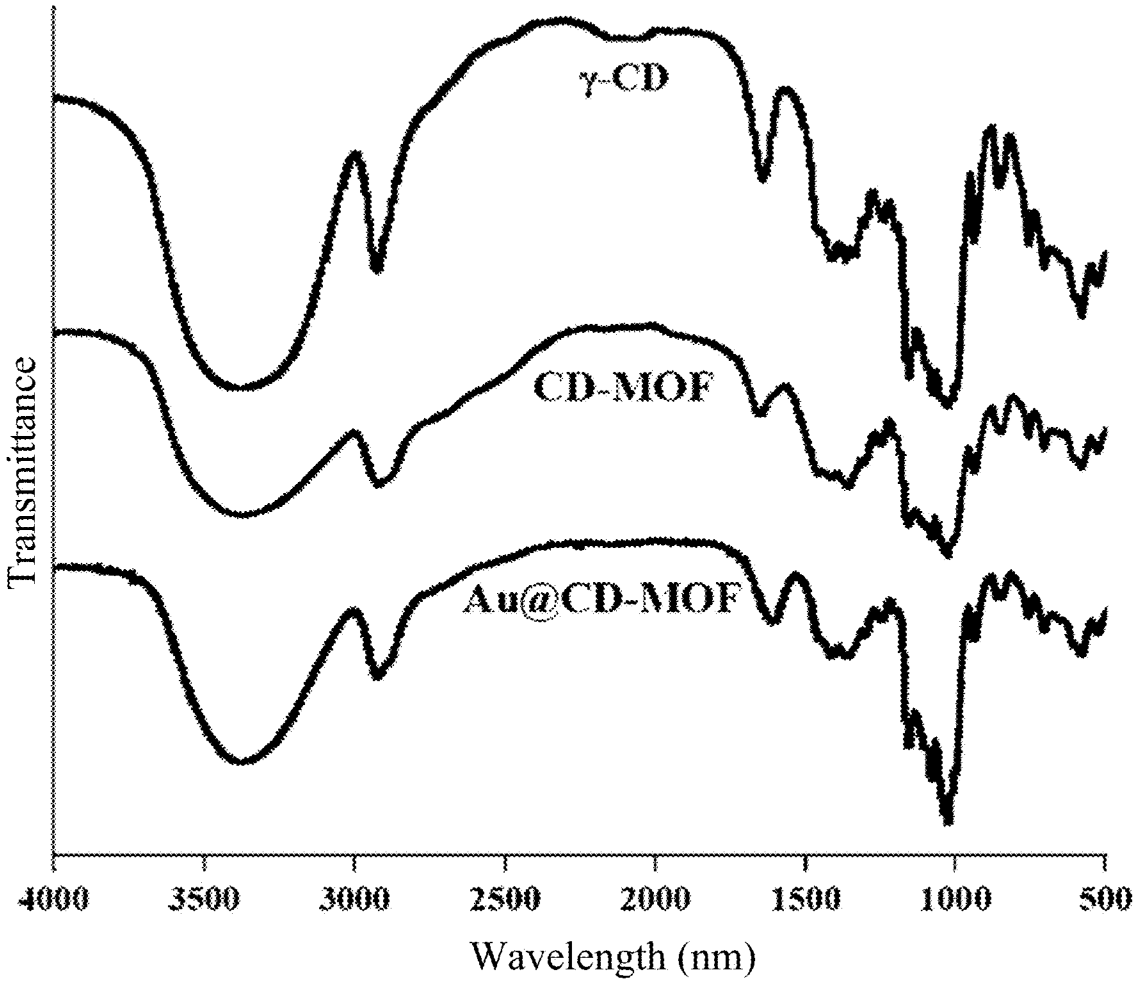
FIG. 8 shows an infrared spectrogram of Au@CD-MOF prepared in Example 15.

FIG. 8 shows an infrared spectrum of Au@CD-MOF prepared in Example 15. The results show that the peak position of Au@CD-MOF is completely consistent with that of CD-MOF, indicating that the structure of CD-MOF is not damaged by the generation of the ultrafine gold nanoparticles within the CD-MOF framework.

Figure 9:
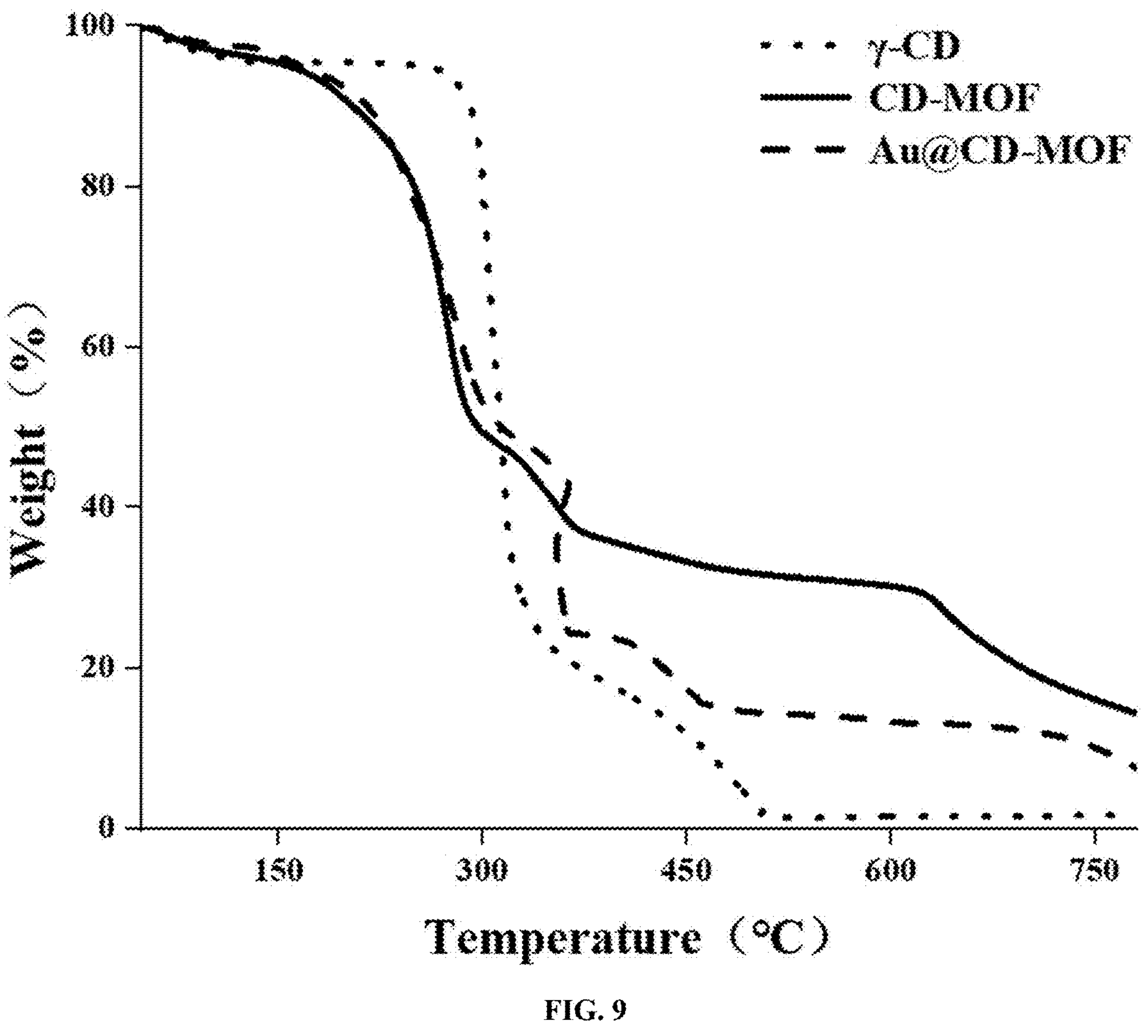
FIG. 9 shows a thermogravimetric diagram of Au@CD-MOF prepared in Example 15.

FIG. 9 shows a thermogravimetric diagram of Au@CD-MOF prepared in Example 15. The results show that the Au@CD-MOF exhibits a better thermal stability than that of free γ-CD at higher than 313° C.

Figure 10:
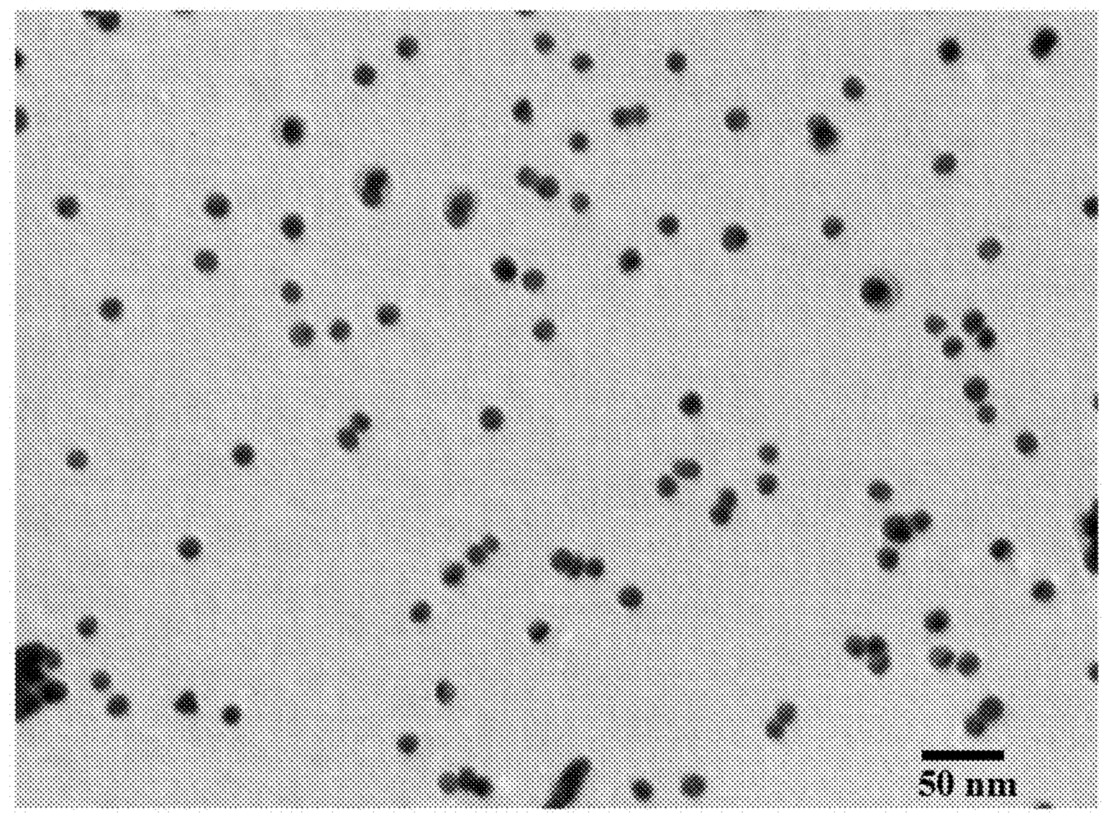
FIG. 10 shows a TEM image of the gold nanoparticles prepared in Comparative Example 1.
Figure 11A:
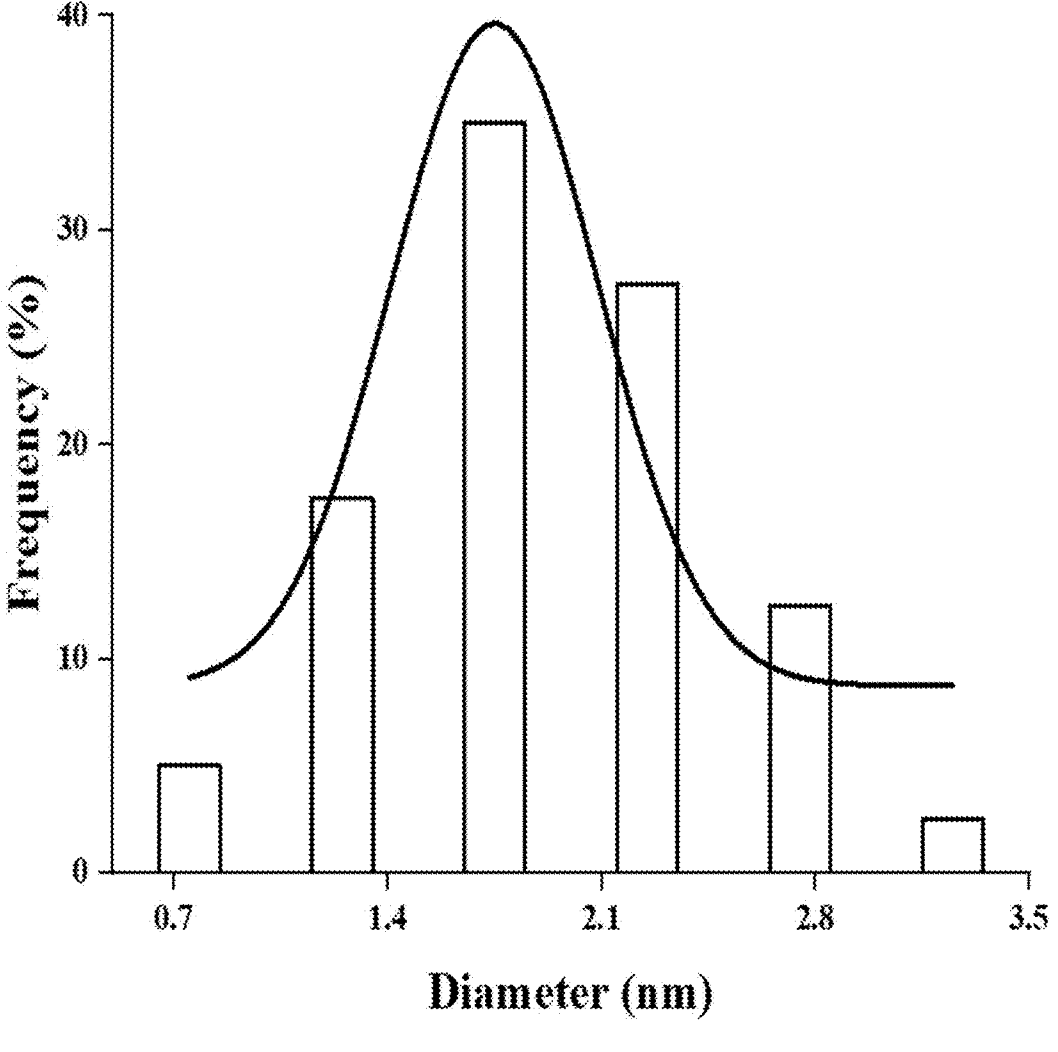
FIG. 11A shows a particle size distribution diagram of the ultrafine gold nanoparticles in Au@CD-MOF prepared in Example 15.
Figure 11B:
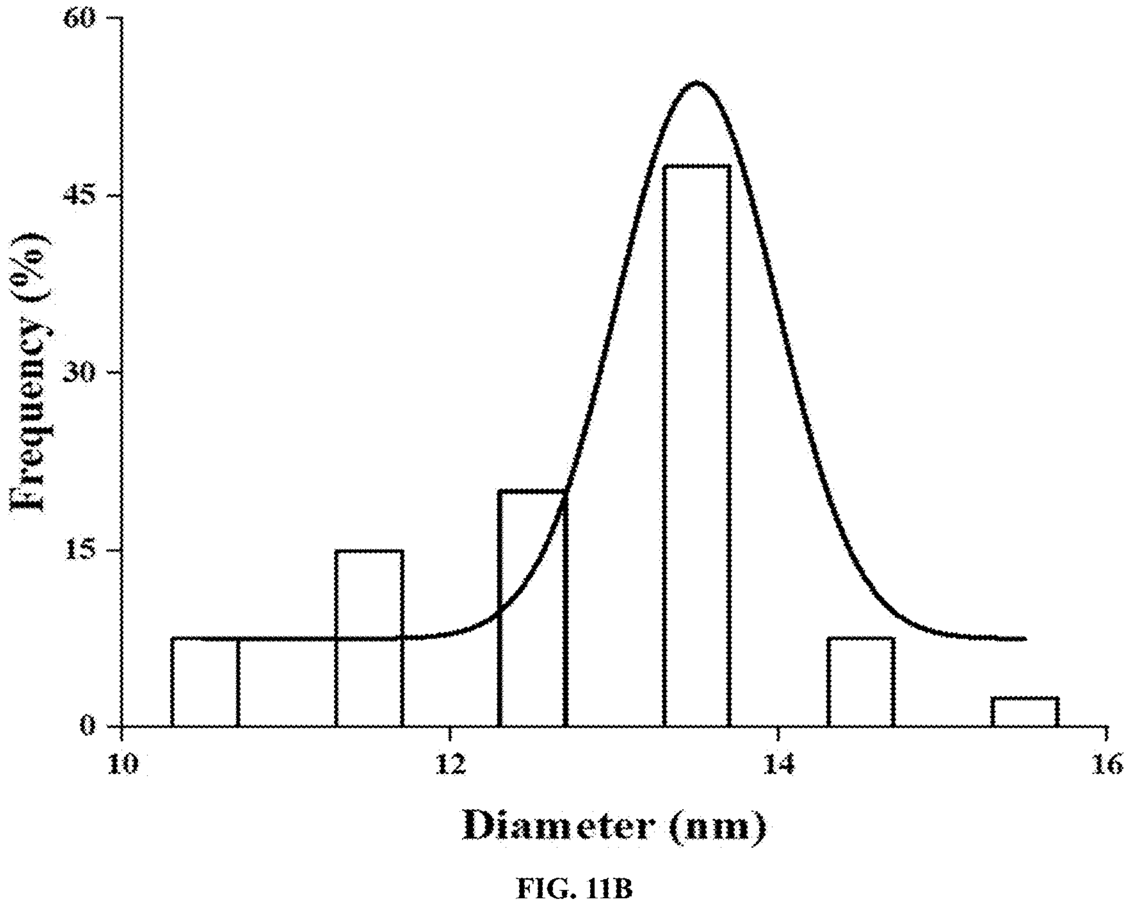
FIG. 11B shows a particle size distribution diagram of the gold nanoparticles prepared in Comparative Example 1.

FIG. 10 shows a TEM image of the gold nanoparticles prepared in Comparative Example 1; FIG. 11A shows particle size distribution of the ultrafine gold nanoparticles in Au@CD-MOF prepared in Example 15; and FIG. 11B shows particle size distribution of the gold nanoparticles prepared in Comparative Example 1. The results showed that the particle size of the ultrafine gold nanoparticles prepared by the method of the present disclosure is mainly distributed at 1 nm to 3 nm, while the particle size of the gold nanoparticles prepared by the traditional method in Comparative Example 1 is mainly distributed at 12 nm to 14 nm.

Test Example 1

Taking *Escherichia coli* (O157: H7) and *Staphylococcus aureus* (ATCC 25923) as examples, the CD-MOF, Au@CD-MOF prepared in Example 15, and common gold nanoparticles (Au) prepared in Comparative Example 1 were tested for their minimum inhibitory concentration (MIC) and the minimum bactericidal concentration (MBC). The specific results were shown in Table 2.

Table 2 Antibacterial results of common gold nanoparticles (Au), CD-MOF, and Au@CD-MOF

| | *E. coli* (O157:H7) | | *S. aureus* (ATCC 25923) | |
|---|---|---|---|---|
| Sample | MIC (μg/mL) | MBC (μg/mL) | MIC (μg/mL) | MBC (μg/mL) |
| Au | >180 | >180 | >180 | >180 |
| CD-MOF | >200000 | >200000 | >200000 | >200000 |
| Au@CD-MOF (based on Au content) | 6.25 | 12.5 | 60 | 80 |

From Table 1, it can be seen that compared with common gold nanoparticles with a particle size mainly distributed at 12 nm and 14 nm, the Au@CD-MOF containing ultrafine gold nanoparticles with a particle size distribution at 1 nm and 3 nm has smaller MIC and MBC. From this, it can be seen that the ultrafine gold nanoparticles show a better antibacterial effect.

The above descriptions are merely preferred embodiments of the present disclosure. It should be noted that a person of ordinary skill in the art may further make several improvements and modifications without departing from the principle of the present disclosure, but such improvements and modifications should be deemed as falling within the scope of the present disclosure.

What is claimed is:

1. A method for preparing an ultrafine gold nanocomposite, comprising the following steps:

mixing a cyclodextrin metal-organic framework (CD-MOF) material, chloroauric acid and a solvent to obtain a mixture; and subjecting the mixture to incubation to obtain the ultrafine gold nanocomposite; wherein the method further comprises, before the mixing, preparing the CD-MOF material by:

mixing γ-cyclodextrin (γ-CD), an alkali metal compound, water and an organic solvent to obtain a mixed material; and subjecting the mixed material to coordination to obtain a coordination product liquid; and mixing the coordination product liquid and a surfactant to obtain an admixture; and subjecting the admixture to crystallization to obtain the CD-MOF material; and an amount of the CD-MOF material is based on an amount of the γ-CD; a molar ratio of the γ-CD to the chloroauric acid is in a range of 5:1 to 7.5:1; and a ratio of an amount of substance of the chloroauric acid to a volume of the solvent is in a range of 1.25 mmol: 1 L to 1.5 mmol: 1 L.

2. The method of claim 1, wherein the incubation is conducted at a temperature of 25° C. to 37° C. for 3 h to 24 h.

3. The method of claim 1, wherein the incubation is conducted under oscillation at a speed of 10 rpm to 240 rpm.

4. The method of claim 1, wherein the incubation is conducted in the dark.

5. An ultrafine gold nanocomposite prepared by the method of claim 1, comprising a CD-MOF material and ultrafine gold nanoparticles loaded on the CD-MOF material.

6. The ultrafine gold nanocomposite of claim 5, wherein the ultrafine gold nanoparticles have a particle size of 1 nm to 3 nm.

7. The ultrafine gold nanocomposite of claim 5, wherein a loading rate of the ultrafine gold nanoparticles in the ultrafine gold nanocomposite is in a range of 0.18 wt % to 2.33 wt %.

8. A method for preparing an antibacterial product, comprising using the ultrafine gold nanocomposite of claim 5.

9. The method of claim 2, wherein the incubation is conducted under oscillation at a speed of 10 rpm to 240 rpm.

10. The method of claim 2, wherein the incubation is conducted in the dark.

11. The ultrafine gold nanocomposite of claim 6, wherein a loading rate of the ultrafine gold nanoparticles in the ultrafine gold nanocomposite is in a range of 0.18 wt % to 2.33 wt %.

* * * * *